United States Patent [19]
Woog et al.

[11] Patent Number: 4,992,419
[45] Date of Patent: Feb. 12, 1991

[54] STABILIZED ERYTHROPOIETIN PREPARATIONS

[75] Inventors: Heinrich Woog, Laudenbach; Werner Gruber, Birkenau; Hans-Jörg Markl, Ellerstadt; Frtiz Demmer, Hirschberg-Leutershausen, all of Fed. Rep. of Germany

[73] Assignee: Boehringer Mannheim GmbH, Mannheim-Waldhof, Fed. Rep. of Germany

[21] Appl. No.: 240,005

[22] Filed: Sep. 1, 1988

[30] Foreign Application Priority Data

May 9, 1987 [DE] Fed. Rep. of Germany ....... 3729863

[51] Int. Cl.$^5$ .............................................. A61K 37/02
[52] U.S. Cl. ......................................... 514/8; 514/12; 514/21; 514/970; 514/971
[58] Field of Search ................ 514/21, 8, 12, 970–971

[56] References Cited

U.S. PATENT DOCUMENTS 3,865,801  2/1975  Chiba .................................. 530/397

FOREIGN PATENT DOCUMENTS 0178665   4/1986  European Pat. Off. .
WO8605096 9/1986  PCT Int'l Appl. .

*Primary Examiner*—F. T. Moezie
*Attorney, Agent, or Firm*—Felfe & Lynch

[57] ABSTRACT

A compatible, storage-stable human protein preparation containing a human protein, a physiologically compatible buffer and optionally complex formers, isotonia-adjusting agents, calcium chloride and other materials usual for injection purposes which, in an injectable form, contains 5 to 50 g./liter urea, 1 to 50 g./liter amino acid and 0.05 to 5 g./liter non-ionic wetting agent. A process for the production of this preparation is also disclosed.

16 Claims, No Drawings

STABILIZED ERYTHROPOIETIN PREPARATIONS

BACKGROUND OF THE INVENTION

The present invention is concerned with stable, non-immunogenic, physiologically readily compatible, dissolved or lyophilised galenical preparations of human proteins and especially of erythropoietin, as well as processes for the preparation thereof.

Human proteins are proteins characteristic of the body which only occur in small amounts, for example, tissue plasminogen activator (tPA), streptokinase, urokinase, interferon, various colony stimulating factors (CSF) and erythropoietin (EPO). The present invention will be explained in more detail using EPO as an example which is preferably used in the formulations.

Erythropoietin (EPO) is a glycoprotein which stimulates the formation of haemoglobin or erythrocytes in the bone marrow. This lipoprotein is mainly formed in the kidneys but is found in very small amounts in the serum and, under physiological conditions, is partly excreted in the urine.

The absence of EPO in the case of kidney insufficiency also causes a renal anaemia. By the administration of EPO in physiological amounts, i.e., a few micrograms, in one or more dosings, the formation of erythrocytes can again be stimulated. Since the body reacts sensitively to small dosage changes, the dosing must be exactly reproducible. EPO is usually injected as an aqueous solution either intramuscularly or intravenously or is administered as a spray via the nasal mucous membrane.

However, it is known that EPO, not only the product first obtained from human urine (Mijake et al., *J. Biol. Chem.* 25, 5558–5564 (1977) but also the product more recently produced by gene technology (WO 85-02610), is not stable in aqueous solution and, even in the case of storage at $-80°$ C., comparatively large activity losses occur. These two known products differ somewhat in their glycosilation pattern and in their activity; a direct comparison with the EPO contained in the serum has hitherto not been known.

These activity losses are to be attributed, on the one hand, to a destruction of the EPO by catalytic effects of the surface of the ampoules used for storage due to traces of heavy metals, atmospheric oxygen and the like, and also, on the other hand, to a deposition of EPO molecules on the vessel wall, a partial denaturing thereof possibly also taking place. Since, as stated above, only a few micrograms are present in each dosage unit, the losses due to adsorption can be considerable, even after a short storage time.

Therefore, European Patent Specification No. 0,178,576 describes the inhibition of this deposition on the vessel wall by the addition of polymeric compounds, such as human or bovine serum albumin, lecithin, dextran, cellulose, polyethylene glycol, and the like, thereby making possible an EPO level of 75 to 98% after about 2 hours storage at 20° C., compared with only 16% without such an addition. However, there was only measured the level of a radioactive labelled ($^{14}C$) product so that these experiments say nothing about the stabilisation of the EPO against decomposition.

However, according to our findings, a long-term stabilisation with such agents cannot be achieved, i.e., the EPO effectiveness in the mouse test decreases strongly and, in addition, these agents can bring about immunogenic reactions when injected.

Furthermore, in European Patent Specification No. 0,178,665 there are disclosed "stabilizers", especially for lyophilised EPO preparations. Besides the polymeric substances PEG 4000, gelatine and dextran 40, there are mentioned various sugars and sugar alcohols, amino acids, inorganic salts and thiol compounds. Combinations of these materials with human serum albumin, gelatine and dextran are also mentioned. In this literature reference, too, there is determined only the level of radioactivities after 2 months storage of the lyophilised products. This is given as being 87 to 99%, in comparison with 60% without any addition. Since the lyophilised material was used directly after the production as a standard, it is not stated how high the activity losses are in the case of the production of the preparations. These preparations also display a high effectiveness loss in the mouse test.

Therefore, there exists the problem of finding a readily compatible EPO preparation which is storage-stable, i.e., ensures the in vivo effectiveness, does not lead to adsorptions on the ampoule and syringe walls, and can easily be made into an injectable form.

SUMMARY OF THE INVENTION

According to the present invention, there is provided a compatible, storage-stable human protein preparation containing a human protein, a physiologically compatible buffer and optionally complex formers, isotonia-adjusting agents, calcium chloride and other materials usual for injection purposes, wherein, in the injection form, the human protein preparation contains 5 to 50 g./liter urea, 1 to 50 g./liter amino acid and 0.5 to 5 g./liter non-ionic wetting agent.

Our investigations have shown that the individual materials either do not possess these desired properties or do so only to a small extent unsuitable for our purposes.

DETAILED DISCLOSURE

Decisive for stabilisation is the addition of urea and of various amino acids. Urea is used in an amount of from 5 to 50 g./liter and preferably of from 10 to 15 g./liter. As amino acids, there may be mentioned, by way of example, glycine, L-alanine, L-arginine, L-isoleucine, L-leucine, L-2-phenylalanine, L-glutamic acid and L-threonine. Mixtures of various amino acids appear to have an especially advantageous effect. The amino acids are unsed therein in amounts of from 0.5 to 50 g./liter and preferably of from 1 to 20 g./liter, the total amount preferably being from 5 to 25 g./liter.

Furthermore, a physiologically compatible buffer is necessary which, in the small concentrations (about 20–100 mMole/liter) necessary for injection solutions, adjusts the pH to a value of from 6.5 to 7.4 and especially of 7.0 to 7.2 necessary for EPO. In addition to phosphate buffers, there can also be used glycinate, carbonate, citrate buffers and the like, in which case, sodium, potassium or ammonium ions can serve as counterion. A buffering action is additionally broughe about by the amino acids present.

The adhesion of the EPO on the ampoule walls and syringes is substantially reduced by the addition of small amounts of a detergent. Since the preparation is preponderantly to be injected, these materials must be physiologically compatible and especially intravenously compatible. Concentrations of from 0.05 to 5 g./liter and especially of from 0.1 to 0.5 g./liter have proved to be useful. Non-ionic wetting agents, such as the various polymacrogol types, especially polyethylene sorbitan laurate (Tween® 20 or 80) and sorbitan trioleate (Span® 35 or 80) and glycerol oleic acid polyglycol ether (Labrafil®) have proved to be useful for this purpose, but other compatible materials can be used in the same way.

In order to reduce the influence of heavy metal ions, which are entrained almost unavoidably in the process of working up the EPO, it has, furthermore, proved to be useful also to add to the solution 0.01 to 5 g./liter of a soluble calcium salt and preferably from about 0.02 to 0.2 g./liter calcium chloride. Other physiologically compatible complex formers, for example, citrate, ethylenediaminetetraacetic acid, nitrilotriacetic acid and pantothenate, can be used.

As solvent, there is used pure water for injection purposes to which, for the production of isotonia, there are also added 0.5 to 10 g./liter sodium chloride or corresponding materials, such as mannitol, sorbitol, and the like.

For the production of the preparations according to the present invention, all adjuvant materials are dissolved in the necessary amount of water, then the EPO preparation, which preferably has an activity of about 100,000 to 200,000 units/mg. protein, is admixed, sterile-filtered into appropriate ampoules, frozen in and gently lyophilised at a low temperature. The preparations obtained can be stored under nitrogen for over 2 years at 0° C. and over 1 year at ambient temperature. In the case of reconstitution with water, they dissolve in a few seconds without turbidity and can thus be injected either directly intravenously or intramuscularly or, after dilution with an isotonic solution, for example aqueous sodium chloride solution, can be infused.

The freezing-in procedure has a special importance. The adjuvant materials are so chosen in nature and amount that the eutectic point of the solution to be frozen in is from −50° to −30° C. With the help of a computer-controlled optimisation programme, there were determined the following optimum conditions for the 3 phases of the lyophilisation:
freezing-in time: 12 to 14 hours at −40° C.;
main drying: brine temperature +10° C., pressure $10^{-1}$ mbar, time 48 to 60 hours;
post-drying: brine temperature +20° C., pressure $10^{-3}$ mbar, time 4 to 6 hours.

It is hereby important to recognize, with the help of a Δp-measurement device, as well as of a conductivity measurement, when the main drying is concluded in order that the product to be lyophilised not be warmed too quickly and that a thawing of the frozen-in solution and consequent activity loss be avoided.

Thus, the adjuvant materials used are so chosen that a uniformly structured ice body to be lyophilised is formed and that, during the lyophilisation, a porous structure (cake) is obtained from which is possible an optimum sublimation of the ice, especially towards the end of the main drying. The post-drying takes place, as mentioned above, at only +20° C. for 4 to 6 hours. This gentle treatment is important since otherwise there is a loss of activity of the material to be lyophilised.

As a rule, the so lyophilised products have a water content of about 2 to 5% according to Karl Fischer. This residual water content depends upon the nature and amount of the adjuvant materials which are used in the formulation in question.

The aqueous solutions of the stabilised EPO can also be filled directly into ampoules and, without lyophilisation, can be made available in a form ready for use. However, the storage stability is thereby shortened, in comparison with the lyophilisate, to about 1 year at 0° C. and to a few months at ambient temperature.

The following examples are given for the purpose of illustrating the present invention:

EXAMPLE 1

Erythropoietin 2000 Units injection dry substance (batch for 35,000 bottles)

In a sterile 100 liter V2A double-mantle kettle provided with stirring means are dissolved the following adjuvant materials:

| | |
|---|---|
| urea | 700.0 g. |
| sodium chloride | 70.0 g. |
| Tween 20 | 7.0 g. |
| sodium dihydrogen phosphate monohydrate | 38.4 g. |
| disodium hydrogen phosphate dihydrate | 350.0 g. |
| calcium chloride dihydrate | 8.4 g. |
| glycine | 105.0 g. |
| L-leucine | 140.0 g. |
| L-isoleucine | 140.0 g. |
| L-threonine | 35.0 g. |
| L-glutamic acid | 35.0 g. |
| L-phenylalanine | 70.0 g. |
| water for injection purposes ad | 70.0 l. |

To 30 liters of this adjuvant material solution are added 214.3 ml. of an erythropoietin crude material batch with an EPO titre of 140,000 Units/ml., then made up to an end volume of 35 liters and stirred. The filtration system used is rinsed with the remaining adjuvant material solution. The batch solution is sterile filtered over a membrane filter of 0.2 μm. pore width. The sterile-filtered solution is filled into 1 ml. injection bottles under aseptic conditions and freeze-dried in a lyophilisation plant under the following criteria:
freezing-in time: 12 to 14 hours at −40° C.;
main drying: brine temperature +10° C., pressure $10^{-1}$ mbar, time 48 to 60 hours;
post-drying: brine temperature +20° C., pressure $10^{-3}$ mbar, time 4 to 6 hours.

There is thus obtained a voluminous, open-pored injection dry substance which is storage-stable for at least 2 years in a refrigerator and for 1 year at ambient temperature and dissolves within a few seconds in 2 ml. water for injection purposes without turbidity and free from particles.

EXAMPLE 2

Erythropoietin lyophilisate 200 Units (batch for 35,000 bottles)

| | |
|---|---|
| ethyropoietin | 46.7 ml. |
| | (7 million Units) |
| sodium chloride | 100.0 g. |
| Tween 20 | 10.0 g. |
| sodium dihydrogen phosphate monohydrate | 155.0 g. |
| disodium hydrogen phosphate dihydrate | 500.0 g. |
| calcium chloride dihydrate | 10.0 g. |
| urea | 1000.0 g. |
| L-leucine | 150.0 g. |
| L-threonine | 120.0 g. |
| L-phenylalanine | 165.0 g. |

| | |
|---|---|
| -continued | |
| water for injection purposes ad | 70.0 l. |

The adjuvant materials are dissolved in 70 liters of water for injection purposes and thereafter divided into two portions of 35 liters. The first 35 liters are mixed with the necessary amount of EPO active material and the second 35 liters are used for rinsing the filtration system used. The batch solution is sterile filtered over a membrane filter of 0.2 μm. pore width. The sterile-filtered solution is filled into 1 ml. injection bottles under aseptic conditions and lyophilised using the same conditions as in Example 1. There is thus obtained a white, porous lyophilisate which is readily soluble in 2 ml. of water and which can be stored for 2 years in a refrigerator or 1 year at ambient temperature without great activity loss.

EXAMPLE 3

Erythropoietin lyophilisate 100 Units (batch for 35,000 bottles)

| | |
|---|---|
| erythropoietin | 233.33 ml. |
| | (35 million Units) |
| sodium chloride | 100.0 g. |
| Tween 20 | 12.0 g. |
| sodium dihydrogen phosphate monohydrate | 140.0 g. |
| disodium hydrogen phosphate dihydrate | 450.0 g. |
| calcium chloride monohydrate | 10.0 g. |
| urea | 700.0 g. |
| glycine | 1050.0 g. |
| L-leucine | 92.0 g. |
| L-glutamic acid | 103.0 g. |
| L-phenylalanine | 115.5 g. |
| water for injection purposes ad | 70.0 l. |

The adjuvant materials are dissolved in 70 liters of water for injection purposes and thereafter divided into two portions of 35 liters. The first 35 liters are mixed with the necessary amount of EPO active material and the second 35 liters are used for rinsing the filtration system used. The batch solution is sterile filtered over a membrane filter of 0.2 μm. pore width. The sterile-filtered solution is filled into 1 ml. injection bottles under aseptic conditions and lyophilised as in Example 1 using the same conditions. There is thus obtained a white, porous lyophilisate which is readily soluble in 2 ml. water and which can be stored for 2 years in a refrigerator or 1 year at ambient temperature without great activity loss.

EXAMPLE 4

Erythropoietin lyophilisate 500 Units (batch for 35,000 bottles)

| | |
|---|---|
| erythropoietin | 116.67 ml. |
| | (17.5 million Units) |
| sodium chloride | 70.0 g. |
| Tween 20 | 7.0 g. |
| sodium dihydrogen phosphate monohydrate | 38.5 g. |
| disodium hydrogen phosphate dihydrate | 490.0 g. |
| calcium chloride dihydrate | 5.6 g. |
| urea | 840.0 g. |
| L-leucine | 92.4 g. |
| L-glutamic acid | 105.0 g. |
| L-phenylalanine | 119.0 g. |
| water for injection purposes ad | 70.0 l. |

The adjuvant materials are dissolved in 70 liters of water for injection purposes and thereafter divided into two portions of 35 liters. The first 35 liters are mixed with the necessary amount of EPO active material and the second 35 liters are used for rinsing the filtration system used. The batch solution is sterile filtered over a membrane filter of 0.2 μm. pore width. The sterile-filtered solution is filled into 1 ml. injection bottles under aseptic conditions and lyophilised as in Example 1 using the same conditions. There is thus obtained a white, porous lyophilisate which is readily soluble in 2 ml. water and which can be stored for 2 years in a refrigerator or 1 year at ambient temperature without great activity loss.

EXAMPLE 5

Erythropoietin lyophilisate 750 Units (batch for 35,000 bottles)

| | |
|---|---|
| erythropoietin | 175.0 ml. |
| | (26.25 million Units) |
| sodium chloride | 100.0 g. |
| Tween 20 | 12.0 g. |
| sodium dihydrogen phosphate monohydrate | 140.0 g. |
| disodium hydrogen phosphate dihydrate | 450.0 g. |
| calcium chloride dihydrate | 10.0 g. |
| glycine | 1250.0 g. |
| L-isoleucine | 98.0 g. |
| L-glutamic acid | 130.0 g. |
| L-phenylalanine | 145.0 g. |
| water for injection purposes ad | 70.0 l. |

The adjuvant materials are dissolved in 70 liters of water for injection purposes and thereafter divided into two portions of 35 liters. The first 35 liters are mixed with the necessary amount of EPO active material and the second 35 liters are used for rinsing the filtration system used. The batch solution is sterile filtered over a membrane filter of 0.2 μm. pore width. The sterile-filtered solution is filled into 1 ml. injection bottles under aseptic conditions and lyophilised as in Example 1 using the same conditions. There is thus obtained a white, porous lyophilisate which is readily soluble in 2 ml. water and which can be stored for 2 years in a refrigerator or for 1 year at ambient temperature without great activity loss.

EXAMPLE 6

In order to test the effectiveness of a various stabilizers, a standard formulation with 1000 U EPO/ml., which contained urea as main stabiliser, was mixed with polyvinylpyrrolidone/protein or with different amino acids and the products were lyophilised. The results obtained are summarized in the following Table 1.

After storing the lyophilisate at 25° C. or 0° C. for 6 weeks, the stability of the EPO was determined as follows in the mouse spleen test according to the procedure of G. Krystal in *Exp Hematol.* 11, 649–660 (1983):

$B_6C_3F_1$ female mice with a body weight of about 20 g. (Zentralinstitut fuer Versuchstierkunde, Hannover, Germany) were injected on two successive days with 60 mg./kg. phenylhydrazine hydrochloride. After 3 further days, the spleen was removed, the spleen cells were suspended in sterile complete medium (Dulbecco Modified Eagle's Medium+584.0 mg./liter L-glutamine+0.1 mMole/liter 2-mercaptoethanol+20% fetal calf serum) and diluted to $4 \times 10^6$ nucleus-containing cells/ml. The suspension, to which had previously been added the test substance or the EPO standard in, in each case, appropriate concentrations, dissolved in BSA buffer, was distributed in microtitre plates (0.2 ml./cup). After incubation (22 hours, 37° C., air+15% carbon dioxide), 20 μl. ³H-methylthymidine solution with 1 uCi per cup were added thereto and again incubated for 2 hours at 37° C. Thereafter, the contents were transferred with the help of a cell harvester and washed with distilled water. The incorporation of ³H-thymidine was determined with a β-scintillation counter and evaluated against the standard preparation.

The lyophilisates to be tested for their EPO activity were first dissolved per ampoule in 2 ml. water for injection purposes, the further dilutions took place, just as in the case of the working standard, with BSA buffer (8.75 g. sodium chloride/1.95 g. calcium chloride dihydrate, 1.00 g. BSA (bovine serum albumin of the firm Calbiochem), water for injection purposes ad 1 liter). ³H-Methylthymidine (specific activity: 2 Ci/mMole) was obtained from New England Nuclear.

TABLE 1

| composition mg./bottle | s1 819892 G | a 819893 H | b 819894 I | ab 819895 K |
|---|---|---|---|---|
| erythropoietin | 1000 U | 1000 U | 1000 U | 1000 U |
| urea | 10.0 | 10.0 | 10.0 | 10.0 |
| sodium chloride | 9.0 | 4.0 | 9.0 | 1.0 |
| Tween 20 | 0.1 | 0.1 | 0.1 | 0.1 |
| Na dihydrogen phosphate × H₂O | 0.55 | 0.55 | 0.55 | 0.55 |
| di-Na hydrogen phosphate × 1H₂O | 5.0 | 5.0 | 5.0 | 5.0 |
| CaCl₂ × 2H₂O | 0.08 | 0.08 | 0.08 | 0.08 |
| Kollidon 12 PF | 5.0 | — | 5.0 | — |
| Gelafundin | 1.0 | 1.0 | — | — |
| glycine | — | 15.0 | — | 15.0 |
| L-leucine | — | — | 2.0 | 2.0 |
| L-isoleucine | — | — | 2.0 | 2.0 |
| L-threonine | — | — | 0.5 | 0.5 |
| L-glutamic acid | — | — | 0.5 | 0.5 |
| L-phenylalanine | — | — | 1.0 | 1.0 |
| water | ad 1.0 ml. | ad 1.0 ml. | ad 1.0 ml. | ad 1.0 ml. |
| stability 25° C. | 493 | 869 | 934 | 1128 |
| stability 0° C. | 985 | 1114 | 1144 | 1205 |

As working standard, there was used the "P009-EPO Standard of Genetics Institute, Cambridge, Mass., U.S.A., which contained 112 U EPO/ml. and 503 ng. protein/ml., equilibrated against the EPO reference standard of WHO "International Reference Preparation of Erythropoietin, Human, Urinary for Bioassay (2nd I.R.P., established 1971)". The standard concentration was in the range of from 10 to 100 mU/ml.

EXAMPLE 7

In the same way as in Example 6, a somewhat modified parent formulation, with 250 U EPO/ml., was mixed with urea and various amino acids or mixtures. For comparison, two mannitol-containing formulations, which corresponded to European Patent Specification No. 0,178,665, were also tested. The results obtained are summarised in the following Table 2.

TABLE 2

| Expt. No. | 895 | 896 | 897 | 898 | 899 | 900 | 901 | 902 | 903 | 904 |
|---|---|---|---|---|---|---|---|---|---|---|
| Composition in mg/ml. | | | | | | | | | | |
| EPO, batch: P007 | 250 U | 250 U | 250 U | 250 U | 250 U | 250 U | 250 U | 250 U | 250 U | 250 U |
| sodium chloride | 1.0 | 1.0 | 1.0 | 1.0 | 1.0 | 1.0 | 1.0 | 1.0 | 1.0 | 1.0 |
| Tween 20 | 0.1 | 0.1 | 0.1 | 0.1 | 0.1 | 0.1 | 0.1 | 0.1 | 0.1 | 0.1 |
| Na dihydrogen phosphate × H₂O | 0.55 | 0.55 | 0.55 | 0.55 | 0.55 | 0.55 | 0.55 | 0.55 | 0.55 | 0.55 |
| di-Na-hydrogen phosphate × 2 H₂O | 5.0 | 5.0 | 5.0 | 5.0 | 5.0 | 5.0 | 5.0 | 5.0 | 5.0 | 5.0 |
| calcium chloride × 2 H₂O | 0.08 | 0.08 | 0.08 | 0.08 | 0.08 | 0.08 | 0.08 | 0.08 | 0.08 | 0.08 |
| mammitol | — | — | — | — | — | — | — | — | — | — |
| urea | — | 10 | — | 10 | — | 10 | — | 10 | — | 10 |
| glycine | 15.0 | — | 15 | — | 15 | — | 15 | — | 15 | — |
| L-leucine (1/100 m molar) | — | — | 1.32 | 1.32 | — | — | 1.32 | 1.32 | — | — |
| L-isoleucine (1/100 m molar) | 1.32 | 1.32 | — | — | 1.32 | 1.32 | — | — | 1.32 | 1.32 |
| L-threonine (1/100 m molar) | — | — | — | — | 1.2 | 1.2 | 1.2 | 1.2 | — | — |
| L-glutamic acid (1/100 m molar) | 1.47 | 1.47 | 1.47 | 1.47 | — | — | — | — | 1.47 | 1.47 |
| L-phenylalanine (1/100 m molar) | — | — | — | — | — | — | — | — | 1.65 | 1.65 |
| L-arginine (1/100 m molar) | 1.74 | 1.74 | 1.74 | 1.74 | 1.74 | 1.74 | 1.74 | 1.74 | — | — |
| NaH₂PO₄ × H₂O | 1.0 | 1.0 | — | 1.0 | 2 | 2 | 2 | 2 | — | — |
| Na₂HPO₄ × 2 H₂O | — | — | — | — | — | — | — | — | 2 | 5 |
| water p.i. ad | 1.0 ml | 1.0 ml | 1.0 ml | 1.0 ml | 1.0 ml | 1.0 ml | 1.0 ml | 1.0 ml | 1.0 ml | 1.0 ml |
| stability 25° C. | 164 | 185 | 150 | 234 | 170 | 229 | 226 | 226 | 229 | 205 |
| stability 0° C. | 182 | 203 | 203 | 242 | 208 | 234 | 232 | 230 | 230 | 167 |
| Expt. No. | 905 | 906 | 907 | 908 | 909 | 910 | 911 | 912 | 982 | 576 | 575 |
| composition in mg/ml. | | | | | | | | | | | |
| EPO, batch: P007 | 250 U | 250 U | 250 U | 250 U | 250 U | 250 U | 250 U | 250 U | 250 U | 250 U | 250 U |
| sodium chloride | 1.0 | 1.0 | 1.0 | 1.0 | 1.0 | 1.0 | 1.0 | 1.0 | 1.0 | 4 | 4 |
| Tween 20 | 0.1 | 0.1 | 0.1 | 0.1 | 0.1 | 0.1 | 0.1 | 0.1 | 0.1 | 0.1 | 0.5 |
| Na dihydrogen phosphate × H₂O | 0.55 | 0.55 | 0.55 | 0.55 | 0.55 | 0.55 | 0.55 | 0.55 | 0.55 | 0.55 | 0.55 |
| di-Na hydrogen phosphate × 2 H₂O | 5.0 | 5.0 | 5.0 | 5.0 | 5.0 | 5.0 | 5.0 | 5.0 | 5.0 | 5.0 | 5.0 |
| calcium chloride × 2 H₂O | 0.08 | 0.08 | 0.08 | 0.08 | 0.08 | 0.08 | 0.08 | 0.08 | 0.08 | 0.08 | 0.08 |
| mannitol | — | — | — | — | — | — | — | — | — | 20 | 30 |

TABLE 2-continued

| | | | | | | | | | | | |
|---|---|---|---|---|---|---|---|---|---|---|---|
| urea | — | 10 | — | 10 | — | 10 | 10 | — | 10 | — | — |
| glycine | 15 | — | 15 | — | 15 | — | 15 | 15 | — | 10 | — |
| L-leucine (1/100 m molar) | 1.32 | 1.32 | — | — | 1.32 | 1.32 | 2 | — | — | — | — |
| L-isoleucine (1/100 m molar) | — | — | 1.32 | 1.32 | — | — | 2 | — | — | — | — |
| L-threonine (1/100 m molar) | — | — | 1.2 | 1.2 | 1.2 | 1.2 | 0.5 | — | — | — | — |
| L-glutamic acid (1/100 m molar) | 1.47 | 1.47 | — | — | — | — | 0.5 | — | — | — | — |
| L-phenylalanine (1/100 m molar) | 1.65 | 1.65 | 1.65 | 1.65 | 1.65 | 1.65 | 1.0 | — | — | — | — |
| L-arginine (1/100 m molar) | — | — | — | — | — | — | — | — | — | — | — |
| NaH$_2$PO$_4$ × H$_2$O | — | — | — | 1 | — | 1 | — | 1 | 1 | — | — |
| Na$_2$HPO$_4$ × 2 H$_2$O | 7 | 5 | — | — | — | — | — | — | — | — | — |
| water p.i. ad | 1.0 ml | 1.0 ml | 1.0 ml | 1.0 ml | 1.0 ml | 1.0 ml | 1.0 ml | 1.0 ml | 1.0 ml | 1.0 ml | 1.0 ml |
| stability 25° C. | 221 | 258 | 205 | 216 | 171 | — | 256 | 175 | 120 | 134 | 97 |
| stability 0° C. | 220 | 291 | 188 | 210 | 197 | 240 | 234 | 218 | 195 | 172 | 178 |

It will be understood that the specification and examples are illustrative but not limitative of the present invention and that other embodiments within the spirit and scope of the invention will suggest themselves to those skilled in the art.

What is claimed is:

1. Compatible, storage-stable erythropoietin preparation comprising erythropoietin, a physiologically compatible buffer, 5 to 50 g/liter urea and 1 to 50 g/liter amino acids.

2. Compatible, storage-stable erythropoietin preparation comprising erythropoietin, a physiologically compatible buffer, 5 to 50 g/liter urea, 1 to 50 g/liter amino acid and 0.05 to 5 g/liter non-ionic wetting agent.

3. An erythropoietin preparation according to claim 1 or 2 further comprising a complex former or an isotonia-adjusting agent.

4. An erythropoietin preparation according to claim 1 or 2 wherein the amino acid is selected from the group consisting of glycine, L-alanine, L-arginine, L-leucine, L-isoleucine, L-2-phenylalanine, L-glutamic acid, L-threonine and mixtures thereof.

5. An erythropoietin preparation according to claim 2 in which the wetting agent is polyethylene sorbitan laurate.

6. An erythropoietin preparation according to claim 3 which comprises calcium chloride as a complex former.

7. An erythropoietin preparation according to claim 3 which comprises sodium chloride as an isotonia-adjusting adjuvent.

8. An erythropoietin preparation according to claim 1 or 2 wherein said phosphate buffer is selected from the group consisting of sodium dihydrogen phosphate, disodium hydrogen phosphate and a mixture thereof.

9. An erythropoietin preparation according to claim 1 or 2 which is in lyophilisized form.

10. An erythropoietin preparation according to claim 3 which is in lyophilisized form.

11. An erythropoietin preparation according to claim 1 or 2 which is in aqueous liquid form.

12. An erythropoietin preparation according to claim 11 which contains, per injection dosage unit of 1 to 5 ml, from 100 to 1 million U of erythropoietin.

13. An erythropoietin preparation according to claim 12 which contains, per injection dosage unit of 1 to 5 ml, from 100 to 20,000 U of erythropoietin.

14. An erythropoietin preparation according to claim 3 which is in aqueous liquid form.

15. An erythropoietin preparation according to claim 14 which contains, per injection dosage unit of 1 to 5 ml, from 100 to 1 million U of erythropoietin.

16. An erythropoietin preparation according to claim 5 which contains, per injection dosage unit of 1 to 5 ml, from 100 to 1 million U of erythropoietin.

* * * * *